United States Patent [19]

Beck

[11] Patent Number: 4,897,981
[45] Date of Patent: * Feb. 6, 1990

[54] METHOD OF PACKAGING INTRAOCULAR LENSES AND CONTACT LENSES

[75] Inventor: Robert E. Beck, Fort Worth, Tex.

[73] Assignee: Alcon Laboratories, Inc., Fort Worth, Tex.

[*] Notice: The portion of the term of this patent subsequent to Apr. 19, 2005 has been disclaimed.

[21] Appl. No.: 946,346

[22] Filed: Dec. 24, 1986

[51] Int. Cl.⁴ .............................................. B65D 81/22
[52] U.S. Cl. ........................................ 53/431; 206/5.1
[58] Field of Search ................... 53/431; 206/5.1, 5.0, 206/438

[56] References Cited

U.S. PATENT DOCUMENTS

| | | | |
|---|---|---|---|
| 3,586,012 | 6/1971 | Paule | 206/5.1 |
| 3,614,959 | 10/1971 | Schollmaier et al. | 206/5.1 |
| 3,621,855 | 11/1971 | Rabinowitz | 206/5.1 |
| 4,254,509 | 3/1981 | Tennant | 3/13 |
| 4,423,809 | 1/1984 | Mazzocco | 206/5.1 |
| 4,444,307 | 4/1984 | Jermyn | 206/5.1 |
| 4,573,998 | 3/1986 | Mazzocco | 623/6 |
| 4,697,697 | 10/1987 | Graham et al. | 206/438 X |
| 4,738,355 | 4/1988 | Jobe | 206/5.1 |

FOREIGN PATENT DOCUMENTS 0136807  4/1986  European Pat. Off. .

Primary Examiner—James F. Coan
Attorney, Agent, or Firm—James A. Arno; Gregg C. Brown

[57] ABSTRACT

A method for packaging intraocular lenses, contact lenses and other small, delicate devices which must be stored in a liquid is described. The method utilizes a container having a conically-shaped compartment to package small, delicate devices (e.G., intraocular lenses) in a manner such that the devices may be easily located in the compartment and removed from the container.

5 Claims, 1 Drawing Sheet

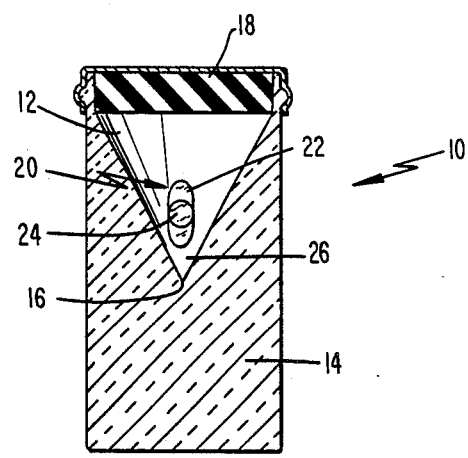

METHOD OF PACKAGING INTRAOCULAR LENSES AND CONTACT LENSES

BACKGROUND OF THE INVENTION

The present invention relates to a method of packaging intraocular lenses and contact lenses, particularly such lenses made from hydrogels or other similar, soft materials. Such intraocular lenses are described in U.S. Pat. Nos. 4,254,509 (Tennant) and 4,573,998 (Mazzocco) and in European Patent Application No. 136,807 (Barrett). Reference is made to these publications for further background concerning intraocular lenses made from hydrogels. Because hydrogels have a relatively high water content, it is normally necessary to store these lenses in a physiologically acceptable, sterile fluid prior to use, so that the lenses do not become dehydrated and brittle. Such storage is also a requirement in connection with the packaging of contact lenses made from hydrogels.

Intraocular lenses are very small, with maximum dimensions (e.g., widths) generally on the order of 15 millimeters or less, and frequently 12 millimeters or less. The small size of these lenses can complicate their removal from a container. More particularly, it can be very difficult to locate the lens in a fluid-filled container and/or grasp the lens and remove it from the container. This difficulty represents a significant problem, since ease of removal of a lens from its container is critical to the convenience of the ophthalmic surgeon and is necessary to facilitate prompt delivery of the lens to the surgeon so that surgical implantation of the lens in the eye of the patient is not delayed or otherwise complicated by difficulties encountered in removing the lens from its container. Similar difficulties are encountered when removing contact lenses from fluid-filled containers.

SUMMARY OF THE INVENTION

A principal objective of the present invention is the provision of a method for packaging intraocular lenses and contact lenses in a manner such that the lenses may be readily located, grasped and removed from their containers.

The foregoing objective and other general objectives of the present invention are achieved by the provision of a method of packaging intraocular lenses and contact lenses which comprises placing the lenses in a container having a lens compartment with a generally conical configuration and filling the compartment to at least a point at which the lens is entirely covered with a physiologically acceptable fluid.

The packaging method of the present invention has several advantages over the use of containers wherein the bottom of the compartment containing the lens is flat. First, the generally conical shape of the lens compartment of the containers utilized in the present invention makes it easier to locate and grasp the lens or lenses contained therein, as compared to prior art containers having a flat bottom surface which allow the lens to assume a horizontal position on the bottom of the container. The configuration of the lens compartment causes the lenses to assume a generally vertical orientation in the container; this orientation facilitates grasping of the lens to easily remove the lens from the container.

BRIEF DESCRIPTION OF DRAWING

The sole FIGURE of drawing is a cross-sectional view of a container of the type utilized in the packaging method of the present invention.

DESCRIPTION OF PREFERRED EMBODIMENT

A container of the type which may be utilized in the present invention 10 is shown in the accompanying drawing. This type of container has been utilized in the chemical field to hold small specimens of solid or liquid materials. These containers, which are generally made from glass, are commercially available (e.g., from Wheaton Scientific, Mays Landing, N.J., U.S.A.). The present invention is based on a new use of these containers in the field of intraocular lens packaging.

The container 10 includes a lens compartment 12 and a solid lower portion 14. The lens compartment 12 has a conical configuration with its apex 16 directed toward the lower portion 14 of the container 10. An intraocular lens 20 is contained in the lower end 26 of the lens compartment 12.

The container 10 is sealed by a cap 18 covering the opening or mouth of the container. In the embodiment illustrated, the cap 18 is comprised of a rubber stopper and an aluminum overseal. The aluminum overseal is secured to a lip around the mouth of the container. Other means for closure, such as a threaded cap which engages with complementary threads around the exterior of the container mouth, are equally acceptable. Still further means for closing the container in a sealed manner will be readily apparent to those skilled in the art.

The intraocular lens 20 may be placed in the container 10 as follows. A physiologically acceptable fluid is placed in the container 10 in an amount sufficient to fill the lens compartment to at least a point at which the lens 20 will be entirely covered when placed therein. The lens is then placed in the lens compartment, additional fluid is added if needed, and the container 10 is sealed by attaching the cap 18 to the mouth of the container. The container and its contents may then be sterilized by means of autoclaving or other suitable sterilization processes.

The intraocular lens 20 may be removed from the container 10 as follows. Prior to removing the cap 18, the lens 20 is visually located in the lens compartment 12. Once the lens 20 is located, it may be necessary to agitate the container if the lens is not moving freely in the fluid in the lens compartment 12. When it is determined that the lens 20 is moving freely in the lens compartment 12, the cap 18 is removed. The lens 20 is then removed by grasping a flange portion 22 of the lens with a sterilized tweezer or other suitable instrument, taking care not to damage the optical portion 24 of the lens.

The packaging method of the present invention is based on the finding that an intraocular lens or contact lens is much easier to remove from a fluid-filled compartment having a conical configuration than from a compartment having a flat bottom surface. This easier removal is directly attributable to the conical configuration of the lens compartment. As can be seen in the drawing, the intraocular lens 20 is positioned in a substantially vertical position in the lens compartment 12. This positioning facilitates removal of the lens 20 from the compartment 12, since it is much easier to grasp the lens with a tweezer or other suitable instrument without damaging the lens if it is in this vertical position rather than in a horizontal position on the flat bottom surface of container.

The present invention has been described above in connection with a preferred embodiment. Obvious variations of that embodiment will be readily apparent to those skilled in the art. For example, the containers of the present invention have been primarily described in connection with packaging of intraocular lenses and contact lenses, but may be equally useful in packing other devices, such as any other medical or nonmedical device which is relatively small, delicate, and required to be packaged in a fluid.

What is claimed is:

1. A method of packaging intraocular lenses and contact lenses, which comprises: placing a lens and a physiologically acceptable fluid in a lens compartment of a container, said compartment having a conical configuration with its apex oriented downwardly towards the bottom of the container so that the lens assumes a substantially vertical position when placed therein, and sealing the container.

2. A method according to claim 1, wherein an intraocular lens is contained in the lens compartment.

3. A method according to claim 2, wherein the intraocular lens is made from a hydrogel.

4. A method according to claim 1, wherein a contact lens is contained in the lens compartment.

5. A method according to claim 4, wherein the contact lens is made from a hydrogel.

* * * * *